US00PP37832P2

(12) United States Plant Patent
Mathey

(10) Patent No.: US PP37,832 P2
(45) Date of Patent: Nov. 3, 2026

(54) ***HYDRANGEA* PLANT NAMED 'SMNHSDE'**

(50) Latin Name: *Hydrangea serrata*
Varietal Denomination: SMNHSDE

(71) Applicant: Spring Meadow Nursery Inc, Grand Haven, MI (US)

(72) Inventor: Megan M. Mathey, Holland, MI (US)

(73) Assignee: Spring Meadow Nursery Inc., Grand Haven, MI (US)

( * ) Notice: Subject to any disclaimer, the term of this patent is extended or adjusted under 35 U.S.C. 154(b) by 0 days.

(21) Appl. No.: 19/370,927

(22) Filed: Oct. 28, 2025

(51) Int. Cl.
*A01H 5/00* (2018.01)
*A01H 6/48* (2018.01)

(52) U.S. Cl.
USPC ..... Plt./250

(58) Field of Classification Search
USPC ..... Plt./250
See application file for complete search history.

*Primary Examiner* — Susan McCormick Ewoldt

(57) ABSTRACT

A new and distinct cultivar of *Hydrangea* plant named 'SMNHSDE' is disclosed, characterized by showy lace-cap inflorescences with large sterile sepals. Sepals are bright reddish-pink with light pink veining. Strongly reblooming with high degree of remontancy. Compact, well-rounded plants with good cold hardiness. The new cultivar is a *Hydrangea*, typically produced as an outdoor ornamental plant.

3 Drawing Sheets

Latin name of the genus and species: *Hydrangea serrata.*
Cultivar denomination: 'SMNHSDE'.

BACKGROUND OF THE INVENTION

The new cultivar is a product of a planned breeding program conducted by the inventor to produce *Hydrangea serrata* cultivars with novel flower colors and forms on plants with compact habits, and good remontancy. The crossing resulting in the new cultivar was made in summer of 2019 at a nursery in Grand Haven, Michigan.

The seed parent is the cultivar *Hydrangea serrata* 'SMNHSI', U.S. Plant Pat. No. 32,548. The pollen parent is the cultivar *Hydrangea serrata* 'SMNHSDD', U.S. Plant Pat. No. 29,832. The new cultivar was found and selected by the inventor in summer of 2019 at the same nursery in Grand Haven, Michigan. Asexual reproduction of the new cultivar 'SMNHSDE' was first performed during summer of 2021 in Grand Haven, Michigan, by softwood cuttings. Through subsequent propagation, multiple additional generations have been reproduced, having shown that the unique features of this cultivar are stable and reproduced true to type.

SUMMARY OF THE INVENTION

The cultivar 'SMNHSDE' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'SMNHSDE'. These characteristics in combination distinguish 'SMNHSDE' as a new and distinct *Hydrangea* cultivar:

1. Showy lace-cap inflorescences with large sterile sepals.
2. Bright reddish-pink sepal color with light pink veining.
3. Strongly reblooming; high degree of remontancy.

4. Compact, well-rounded habit.
5. Good cold hardiness.

PARENT COMPARISONS

Plants of 'SMNHSDE' are similar to plants of the seed parent in most horticultural characteristics, however, plants of 'SMNHSDE' differ in the following:

1. The upper surface of mature Sepals of the infertile flowers of the new cultivar are Red-Purple 70C with Red-Purple 70D venation in basic soil conditions, while the sepals of the seed parent are Red-Purple 73A and 69D in basic soil conditions.

Plants of 'SMNHSDE' are similar to plants of the pollen parent in most horticultural characteristics, however, plants of 'SMNHSDE' differ in the following:

1. Sepals of the new cultivar occur in a single whorl; the sepals of the pollen parent are in a fully double whorl.
2. Sterile flowers of the new cultivar are smaller but more abundant, while the sterile flowers of the pollen parent are larger but less abundant.
3. Sepal color of the new cultivar is more vibrant than the sepal color of the pollen parent.
4. Sepals of the new cultivar do not reliably turn clear blue in acidic soil, while sepals of the pollen parent reliably turn a clear, light blue in acidic soil.

COMMERCIAL COMPARISON

Plants of 'SMNHSDE' can be compared to plants of the commercial cultivar *Hydrangea serrata* 'MAK20', U.S. Plant Pat. No. 24,820. Plants of 'SMNHSDE' are similar to plants of 'SMNHAGOV' in most horticultural characteristics, however, plants of 'SMNHSDE' differ in the following:

1. Sepal apex of the infertile flowers of the new cultivar is broadly acute, while the sepal apex of this comparator is rounded/obtuse.

2. the infertile flowers of the new cultivar are single, while the sepals of this comparator are semi-double.
3. Plant habit of the new cultivar is more compact than the plant habit of this comparator.
4. Sepal color of the infertile flowers of the new cultivar is more vibrant than the sepal color of this comparator.
5. Sepals of the infertile flowers of the new cultivar do not reliably turn clear blue in acidic soil, while sepals of this comparator do reliably turn clear blue in acidic soil

BRIEF DESCRIPTION OF THE PHOTOGRAPHS

The accompanying photograph in FIG. 1 illustrates a plant of 'SMNHSDE' grown outdoors, in the ground in Grand Haven, Michigan. This plant is about 4 to 5 years old.

Figure 1:
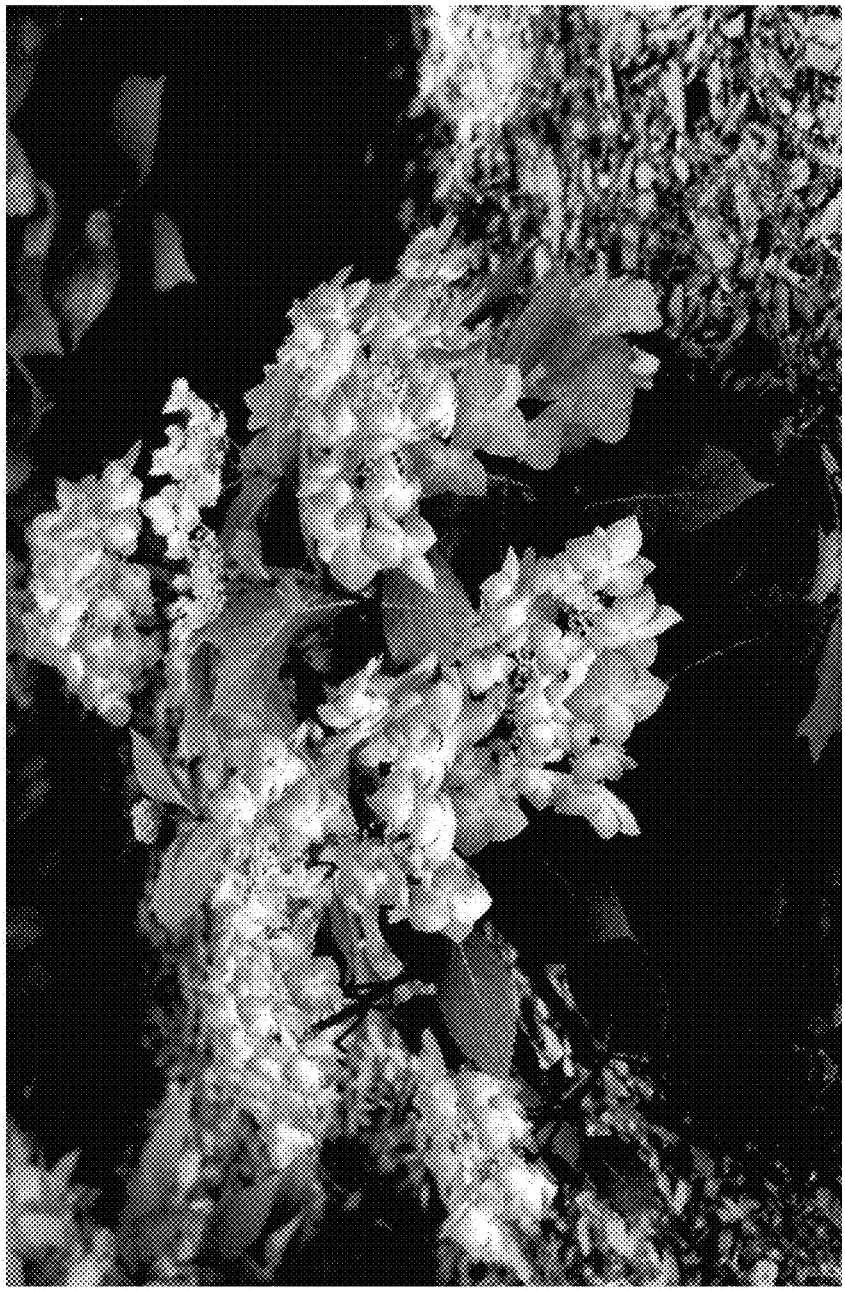
Figure 2:
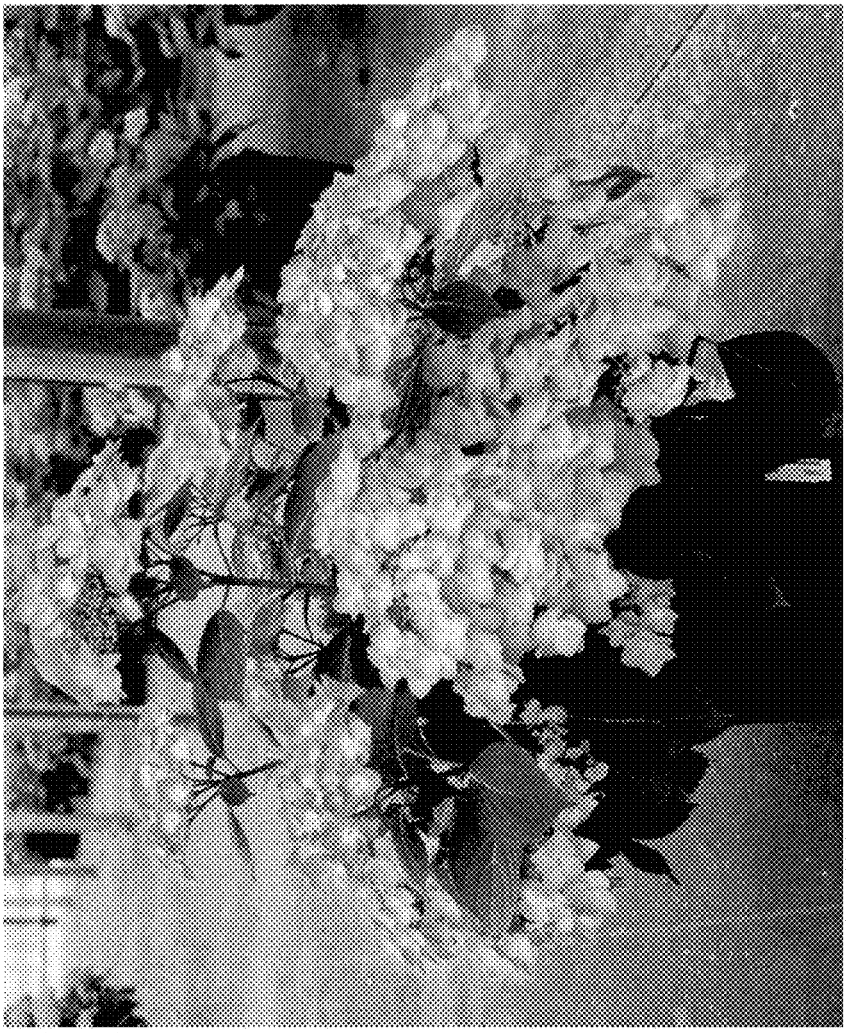
FIG. 2 illustrates in full color a typical plant of 'SMNHSDE' grown in a poly-greenhouse in Grand Haven, Michigan. This plant is approximately 2 to 3 years old, grown in a 5-gallon pot.
Figure 3:
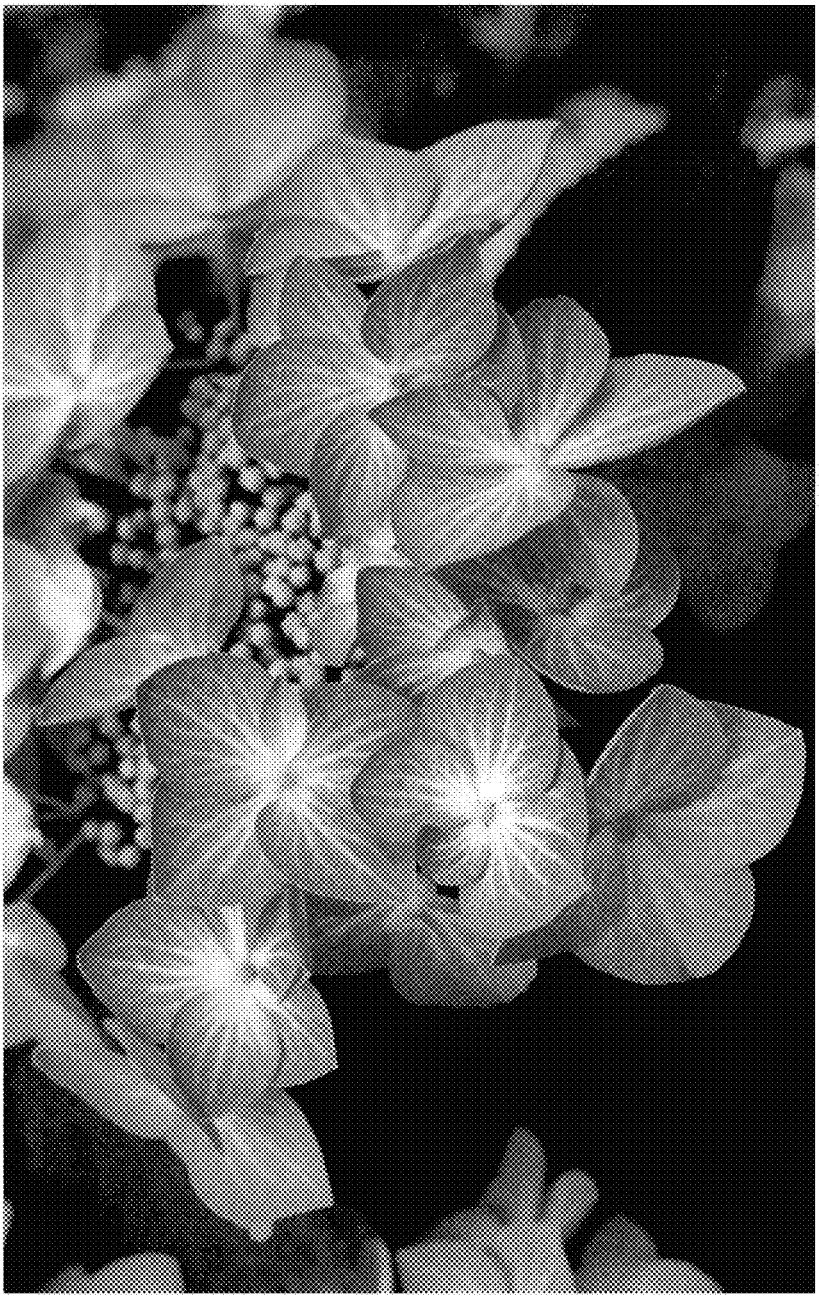
FIG. 3 illustrates in full color a close up of an inflorescence of 'SMNHSDE' which is not quite fully mature.

The photographs were taken using conventional techniques and although colors may appear different from actual colors due to light reflectance it is as accurate as possible by 16 conventional photographic techniques.

DETAILED BOTANICAL DESCRIPTION

In the following description, color references are made to The Royal Horticultural Society Colour Chart 2015, except where general terms of ordinary dictionary significance are used. The following observations and measurements describe 'SMNHSDE' plants grown in a poly-greenhouse in Grand Haven, Michigan. The plants were 3 to 4 years old. Temperatures ranged from 5° C. to 10° C. at night to 18° C. to 27° C. during the day. No artificial light, photoperiodic treatments were given to the plants. Measurements and numerical values represent averages of typical plant types. Botanical classification: *Hydrangea serrata* 'SMNHSDE'.

PROPAGATION

Typical method: Softwood cuttings.
Root initiation: 10 days in summer.
Time to produce rooted cutting: About 30 days in summer.
Roots: Medium to thick, moderate-freely branching, fibrous, moderately dense. White in color, not accurately measured with R.H.S. chart.

PLANT

Growth habit: Compact, rounded.
Shape: Globose.
Height: 50 cm.
Plant spread: 90 cm.
Pot size of plant described: 5-gallon root pouch.
Age of plant described: 3 to 4 years.
Growth rate: Moderate to high.
Plant vigor: High.
Stem:
- *Branching*.—Basal and freely.
- *Pinching*.—Some required to encourage well-rounded habit.
- *Number of lateral branches*.—About 60.
- *Shape*.—Rounded with lenticels.
- *Color*.—Immature: RHS Yellow-Green 144A with Brown 200A lenticels. Mature: Near RHS Grey-Brown 199B.
- *Length*.—40 cm.
- *Width*.—4 mm.
- *Aspect*.—0° to 30° from vertical.
- *Strength*.—Moderate to high.
- *Pubescence*.—Slight, on new growth only.
- *Internode length*.—3.5 cm.

FOLIAGE

Leaf:
- *Arrangement*.—Opposite.
- *Shape*.—Elliptic to obovate.
- *Length*.—12 cm.
- *Width*.—5 cm.
- *Apex*.—Broadly acuminate.
- *Base*.—Cuneate.
- *Margin*.—Serrate.
- *Texture of top surface*.—Glabrous; coriaceous.
- *Texture of bottom surface*.—Glabrous; coriaceous.
- *Pubescence*.—None.
- *Color*.—Young Foliage, Upper Side: RHS Green NN137A. Young Foliage, Under Side: RHS Yellow-Green 147B. Mature Foliage, Upper Side: RHS Green NN137A. Mature Foliage, Under Side: RHS Yellow-Green 147B.

Venation:
- *Type*.—Pinnate.
- *Color*.—Mature, Upper Side: RHS Yellow-Green 144A. Mature, Under Side: RHS Yellow-Green 144A.

Petiole:
- *Length*.—1.5 cm.
- *Width*.—2 mm.
- *Color*.—Upper Side: RHS Yellow-Green 144A. Under Side: RHS Yellow-Green 144A.
- *Texture*.—Upper Side: Glabrous. Under Side: Glabrous.

INFLORESCENCE

Natural flowering season: Summer.
Inflorescence type: Lacecap.
Panicle:
- *Shape*.—Compound umbel; flat-topped.
- *Height*.—7 cm.
- *Diameter*.—16 cm.
- *Longevity*.—2 to 3 weeks.

Fragrance: None.
Sterile flowers:
- *Flowers per inflorescence*.—25 to 30.
- *Aspect*.—Upright and outward.
- *Shape*.—Rotate.
- *Length*.—3.5 cm.
- *Diameter*.—3.5 cm.
- *Depth*.—0.5 cm.
- *Persistence*.—Persistent.
- *Longevity*.—2 to 3 weeks.

Bud:
- *Length*.—3 mm.
- *Diameter*.—3 mm.
- *Shape*.—Globose.
- *Color*.—Acidic: RHS Violet-Blue 98C. Basic: RHS Purple 75A and 75B.

Petals:
*Number.*—4 to 5.
*Arrangement.*—Cruciform or stellate.
*Shape.*—Elliptic.
*Tip.*—Broadly acute.
*Base.*—Broadly cuneate.
*Margin.*—Entire.
*Length.*—3 mm.
*Width.*—2 mm.
*Texture.*—Upper side: Glabrous. Under side: Glabrous.
*Color.*—When Opening, Upper Side: Acidic: RHS Violet-Blue 98C. Basic: RHS Purple 75A and 75B. When Opening, Under Side: Acidic: RHS Violet-Blue 98C. Basic: RHS Purple 75A and 75B. Fully Opened, Upper Side: Acidic: RHS Violet-Blue 98C. Basic: RHS Purple 75A and 75B. Fully Opened, Under Side: Acidic: RHS Violet-Blue 98C. Basic: RHS Purple 75A and 75B.

Sepals:
*Number.*—4 to 5.
*Arrangement.*—Cruciform to stellate.
*Shape.*—Ovate.
*Tip.*—Broadly acute.
*Base.*—Obtuse.
*Margin.*—Entire.
*Length.*—2 cm.
*Width.*—1.5 cm.
*Texture.*—Upper side: Glabrous, silky. Under side: Glabrous, silky.
*Color.*—When Opening, Upper Side: Acidic: RHS Purple N75A. Basic: RHS Red-Purple 60D with White 155A venation and base. When Opening, Under Side: Acidic: RHS Purple N75A. Basic: RHS Red-Purple 63C. Fully Opened, Upper Side: Acidic: RHS Purple 75A. Basic: RHS Red-Purple 70C with Red-Purple 70D venation. Fully Opened, Under Side: Acidic: RHS Purple 75A. Basic: RHS Red-Purple 70C.

Pedicel:
*Length.*—2 cm.
*Diameter.*—2 mm.
*Angle.*—45° relative to peduncle.
*Strength.*—Moderate.
*Texture.*—Slightly pubescent.
*Color.*—Acidic: Closest to RHS Violet-Blue 97A with Purple N77A lenticels. Basic: Closest to RHS Greyed-Yellow 162D with Red-Purple 63C lenticels.

Fertile flowers:
*Flowers per inflorescence.*—300 to 400.
*Aspect.*—Upright.
*Shape.*—Rotate.
*Length.*—7 mm.
*Diameter.*—7 mm.
*Depth.*—5 mm.
*Persistence.*—Self-cleaning.
*Longevity.*—1 week on plant.

Bud:
*Length.*—3 mm.
*Diameter.*—3 mm.
*Bud shape.*—Globose.
*Bud color.*—Acidic: RHS Violet-Blue 98C. Basic: RHS Violet-Blue 75A and 75B.

Petals:
*Number per flower.*—6.
*Arrangement.*—Whorl.
*Shape.*—Elliptic.
*Tip.*—Acute.
*Base.*—Cuneate.
*Margin.*—Entire.
*Length.*—3 mm.
*Width.*—1.5 mm.
*Texture.*—Upper Side: Glabrous. Under Side: Glabrous.
*Color.*—When Opening, Upper Side: Acidic: RHS Violet-Blue 98C. Basic: RHS Purple 75A and 75B. When Opening, Under Side: Acidic: RHS Violet-Blue 98C. Basic: RHS Purple 75A and 75B. Fully Opened, Upper Side: Acidic: RHS Violet-Blue 98C. Basic: RHS Purple 75A and 75B. Fully Opened, Under Side: Acidic: RHS Violet-Blue 98C. Basic: RHS Purple 75A and 75B.

Sepals: Sepals are inconspicuous too small to be accurately measured.

Pedicel:
*Length.*—5 mm.
*Diameter.*—1 mm.
*Angle.*—45° relative to peduncle.
*Strength.*—Moderate.
*Texture.*—Glabrous.
*Color.*—Acidic: Closest to RHS Violet-Blue 97A. Basic: Closest to RHS Greyed-Yellow 162D.

REPRODUCTIVE ORGANS

Sterile flower:
Stamens:
*Number.*—6 to 10.
*Filament length.*—3 mm.
*Filament color.*—Acidic: RHS Violet-Blue 96B. Basic: RHS Red-Purple 70C.

Anthers:
*Shape.*—Globose.
*Length.*—1 mm.
*Color.*—Acidic: RHS Violet-Blue 98C. Basic: RHS Red-Purple 75A and 75B.
*Pollen amount.*—Sparse.
*Pollen color.*—RHS Yellow 4D.

Pistil:
*Number.*—1.
*Length.*—2 mm.

Stigma:
*Shape.*—3-lobed.
*Color.*—Acidic: RHS Yellow-Green 145D. Basic: RHS Yellow-Green 145D.
*Style length.*—2 mm.
*Style color.*—Acidic: RHS Violet-Blue 96B. Basic: RHS Violet-Blue 94B.
*Ovary color.*—Acidic: RHS Violet-Blue 96B. Basic: RHS Violet-Blue 94B.

Fertile flower:
Stamens:
*Number.*—10.
*Filament length.*—4 mm.
*Filament color.*—Acidic: RHS Violet-Blue 96B. Basic: RHS Red-Purple 70C.

Anthers:
*Shape.*—Globose.
*Length.*—1 mm.
*Color.*—Acidic: RHS Violet-Blue 98C. Basic: RHS Red-Purple 75A and 75B.

*Pollen amount*.—Sparse.
*Pollen color*.—RHS Yellow 4D.
Pistil:
*Number*.—1.
*Length*.—5 mm.
Stigma:
*Shape*.—Rounded.
*Color*.—Acidic: RHS Yellow-Green 145D. Basic: RHS Yellow-Green 145D.
*Style length*.—3 mm.
*Style color*.—Acidic: RHS Violet-Blue 96B. Basic: RHS Violet-Blue 94B.
*Ovary color*.—Acidic: RHS Violet-Blue 96B. Basic: RHS Violet-Blue 94B.

SEEDS

Quantity: Approximately 10 per fertile flower.
Shape: Narrowly-elliptic or sickle-shaped.
Length: Less than 1 mm.
Diameter: Less than 1 mm.
Color: RHS Brown 200A.

OTHER CHARACTERISTICS

Fruit: Not observed.
Disease resistance: Resistant to leaf spot, powdery mildew, and botrytis blight. No other resistance nor susceptibility to normal diseases and pests of *Hydrangea* observed.
Environmental tolerance: Tolerant to wind and rain.
Temperature tolerance: Hardy to USDA Zones 4 to 9.

What is claimed is:

1. A new and distinct cultivar of *Hydrangea* plant named 'SMNHSDE' as herein illustrated and described.

* * * * *